(12) United States Patent
Heismann (10) Patent No.: US 9,439,618 B2
(45) Date of Patent: Sep. 13, 2016

(54) METHOD FOR GENERATING A PET OR SPECT IMAGE DATASET AND HYBRID IMAGING MODALITY FOR THIS PURPOSE

(71) Applicant: SIEMENS AKTIENGESELLSCHAFT, Munich (DE)

(72) Inventor: Björn Heismann, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 117 days.

(21) Appl. No.: 14/165,609

(22) Filed: Jan. 28, 2014

(65) Prior Publication Data
US 2014/0217293 A1    Aug. 7, 2014

(30) Foreign Application Priority Data
Feb. 5, 2013    (DE) .................. 10 2013 201 822

(51) Int. Cl.
*A61B 6/00*    (2006.01)
*G06T 7/20*    (2006.01)
(Continued)

(52) U.S. Cl.
CPC .......... *A61B 6/5264* (2013.01); *A61B 6/4417* (2013.01); *G01T 1/1603* (2013.01); *G01T 1/1663* (2013.01); *G01T 1/2985* (2013.01); *G06T 7/20* (2013.01)

(58) Field of Classification Search
CPC   A61B 6/5264; A61B 6/4417; G01T 1/1603; G01T 1/1663; G01T 1/2985
See application file for complete search history.

(56) References Cited

U.S. PATENT DOCUMENTS

2003/0004405 A1*  1/2003  Townsend ............ A61B 6/032
                                                  600/407
2004/0114708 A1*  6/2004  Bruder ................ A61B 6/4028
                                                  378/4
(Continued)

FOREIGN PATENT DOCUMENTS

DE    102005017492 A1    10/2006
DE    102005023907 A1    12/2006
DE    102007009182 A1     8/2008

OTHER PUBLICATIONS

Fahey, F.H., "Data Acquisition in PET Imaging", J Nucl Med Technol 2002; 30:39-49.
(Continued)

*Primary Examiner* — David Porta
*Assistant Examiner* — Jeremy S Valentiner
(74) *Attorney, Agent, or Firm* — Harness, Dickey & Pierce, P.L.C.

(57) ABSTRACT

A method is disclosed for generating a PET or SPECT image dataset. In an embodiment, the method includes acquiring a plurality of PET or SPECT measurement signals from an examination region; acquiring a plurality of anatomy image datasets that show the examination region using a second imaging modality at the same time as acquiring the PET or SPECT measurement signals; determining the similarity of a reference anatomy image dataset acquired at a time point t' using the second imaging modality to at least one anatomy image dataset acquired at a different time point and/or predetermining a temporal weighting function; and generating a PET or SPECT image dataset taking into account the similarity of the anatomy image datasets and/or weighting the PET measurement signals temporally. A hybrid imaging modality is also disclosed.

28 Claims, 4 Drawing Sheets

(51) Int. Cl.
*G01T 1/166* (2006.01)
*G01T 1/29* (2006.01)
*G01T 1/16* (2006.01)

(56) References Cited

U.S. PATENT DOCUMENTS

| | | | |
|---|---|---|---|
| 2005/0053196 A1* | 3/2005 | Mostafavi | 378/98.12 |
| 2005/0253076 A1* | 11/2005 | Wollenweber | G01T 1/2985 250/363.09 |
| 2006/0002615 A1* | 1/2006 | Fu | A61B 6/5235 382/254 |
| 2006/0235295 A1* | 10/2006 | Boese et al. | 600/428 |
| 2006/0266947 A1* | 11/2006 | Krieg et al. | 250/363.04 |
| 2008/0193003 A1* | 8/2008 | Shechter | A61B 6/032 382/131 |
| 2008/0219510 A1* | 9/2008 | Martin et al. | 382/107 |
| 2009/0003655 A1* | 1/2009 | Wollenweber | 382/107 |
| 2009/0037130 A1* | 2/2009 | Feiweier | A61B 6/032 702/104 |
| 2009/0041318 A1* | 2/2009 | Feiweier et al. | 382/128 |
| 2009/0076379 A1* | 3/2009 | Hamill et al. | 600/424 |
| 2010/0046821 A1* | 2/2010 | Manjeshwar | A61B 6/037 382/131 |
| 2011/0116695 A1* | 5/2011 | Wollenweber | A61B 6/469 382/131 |
| 2012/0281897 A1* | 11/2012 | Razifar et al. | 382/131 |
| 2013/0131493 A1* | 5/2013 | Wollenweber | A61B 5/055 600/411 |

OTHER PUBLICATIONS

German Office Action for priority application DE 10 2013 201 822.3 dated Aug. 27, 2013.
German priority application DE 10 2013 201 822.3, filed Feb. 5, 2013.

* cited by examiner

METHOD FOR GENERATING A PET OR SPECT IMAGE DATASET AND HYBRID IMAGING MODALITY FOR THIS PURPOSE

PRIORITY STATEMENT

The present application hereby claims priority under 35 U.S.C. §119 to German patent application number DE 102013201822.3 filed Feb. 5, 2013, the entire contents of which are hereby incorporated herein by reference.

FIELD

At least one embodiment of the present invention generally relates to a method and/or a hybrid imaging modality for generating a PET or SPECT image dataset.

BACKGROUND

Positron emission tomography, PET for short, is an imaging method for showing the spatial distribution of a radioactive substance in an examination object. The radioactive substance used is a positron-emitting radionuclide. On collision with an electron the emitted positrons are converted to two photons moving away from one another in opposing directions. These are detected using a detector ring disposed around the examination object. If detection takes place within a predetermined time segment, this is judged to be a coincidence and therefore an annihilation event. The line connecting the detecting segments of the detector ring is referred to as the line of response or LOR for short. As the distance between positron emission and collision is short, it is determined that the emission source, in other words a point where parts of the radionuclide are located, is on or close to a LOR.

An individual annihilation event or a single LOR does not permit conclusions about a spatial distribution. It is only possible to calculate a positron emission tomography image dataset from the individual LORs by recording a number of annihilation events. The LORs can also be shown graphically in the time sequence in which they occurred in the form of a so-called sinogram. The precise calculation of a sinogram and the determination of a positron emission tomography image dataset therefrom is described for example in Fahey F. H., Data Acquisition in PET Imaging, J Nucl Med Technol 2002; 30:39-49.

In the following, the acquisition of a positron emission tomography image dataset refers to the spatially resolved recording of annihilation events with subsequent calculation of the positron emission tomography image dataset.

The acquisition time varies as a function of the radioactivity of the radionuclide and the desired signal intensity but it is approximately at least one minute.

Such acquisition times give rise to the problem of the examination region or examined patient moving. The emission source in the form of the radionuclide, which is generally packaged as a radiopharmaceutical and has been metabolized, is then of course also displaced so the determined positron emission tomography image dataset is blurred. Such blurring is therefore a motion artifact.

To avoid blurring it is known to acquire anatomy image datasets using a magnetic resonance device or computed tomography device parallel to the PET measurement. The image datasets are then used to calculate displacement vectors, which are transferred to the LORs in order to minimize the motion artifacts.

However this procedure is relatively time-consuming and computation-intensive, which is why a "real time" reconstruction of a positron emission tomography image dataset is not performed in this manner. It is however desirable for example when performing interventions.

The designs and embodiments also always apply similarly to single photon emission computed tomography (SPECT) acquisitions and image datasets. In contrast to PET, gamma emitters are used, which are detected with collimators. There are further differences, which are however generally not of relevance in respect of the inventive method. Reference is therefore made primarily to PET in the following for the sake of simplicity.

SUMMARY

At least one embodiment of the present invention is directed to a method and a hybrid imaging modality which can be used to calculate positron emission tomography image datasets or SPECT image datasets with fewer motion artifacts with less computation outlay.

According to at least one embodiment of the invention, a method for generating a PET or SPECT image dataset is disclosed. Advantageous developments of the invention are set out in the dependent claims.

According to at least one embodiment of the invention, anatomy image datasets are acquired using a second modality parallel to the acquisition of the PET measurement signals with a positron emission tomography device. These do not have to image the identical examination region in respect of the PET measurement signals, nor do they have to have identical resolutions, slice thicknesses or the like. The anatomy image datasets only have to overlap with the PET measurement signals in the imaged part of the examination object in which a combination of the respective types of information is deemed necessary.

At least one embodiment of the present invention is also directed to a hybrid imaging modality. This comprises a positron emission tomography device and at least one second imaging modality, in particular a magnetic resonance device and/or a computed tomography device, as well as a control facility, which may be configured to perform at least one embodiment of the method.

The implementation of the abovementioned embodiments of the method in the control apparatus can be effected as software or as (permanently wired) hardware.

The advantageous embodiments of the inventive method correspond to corresponding embodiments of the inventive hybrid imaging modality, therefore please refer to the corresponding method features and their advantages to avoid unnecessary repetitions.

BRIEF DESCRIPTION OF THE DRAWINGS

Further advantages, features and particularities of the present invention will emerge from the description which follows of advantageous embodiments of the invention.

In the drawing

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to at least one embodiment of the invention, anatomy image datasets are acquired using a second modality parallel to the acquisition of the PET measurement signals with a positron emission tomography device. These do not have to image the identical examination region in respect of the PET measurement signals, nor do they have to have identical resolutions, slice thicknesses or the like. The anatomy image datasets only have to overlap with the PET measurement signals in the imaged part of the examination object in which a combination of the respective types of information is deemed necessary.

The anatomy image datasets of the second imaging modality are preferably acquired with identical parameters, to avoid complex postprocessing steps. It is however possible for example to reduce the resolution, without noticeably delaying the evaluation.

The second imaging modality can be in particular a computed tomography device or a magnetic resonance device, as there are already hybrid imaging modalities including a positron emission tomography device and a computed tomography device or a magnetic resonance device and such hybrid devices do not require registration of the respective image data or the operation is highly simplified.

In order to determine a positron emission tomography image dataset with fewer motion artifacts at any measurement time point t' of the PET measurement, an anatomy image dataset acquired at this measurement time point t', referred to in the following as the reference anatomy image dataset, is used. Similarity with the reference anatomy image dataset is then determined for at least some of the further anatomy image datasets acquired parallel to the PET measurement. Only the measurement signals, for which the associated anatomy image dataset is similar to the reference anatomy image dataset, are then used to produce the positron emission tomography image dataset.

The term similarity generally defines a continuous or fluid value. In the present application the determination of the similarity of the anatomy image dataset to the reference anatomy image dataset can also mean that a value describing the similarity or a number of values describing the similarity is/are above or below one or more threshold values. The values above this threshold value can then be determined continuously. However the threshold value can also be an exclusion criterion, in which case there are only anatomy image datasets that are similar and not similar to the reference anatomy image dataset and further differentiation is not required in this embodiment due to use as an exclusion criterion for PET measurement signals.

This means that all measurement signals for which movement is "too great" compared with the reference anatomy image dataset are filtered out. All the others are weighted in respect of the similarity of the anatomy image dataset to the reference anatomy image dataset.

As an alternative or in addition to weighting by means of similarity the PET or SPECT measurement signals can be multiplied by a temporal weighting function. This can be a rectangular function or a Gaussian function. In the case of additive weighting the PET or SPECT signals are filtered twice, once in respect of the similarity of the corresponding anatomy image dataset, in other words the one acquired at the measurement time point of the measurement signal, to the reference anatomy image dataset and secondly temporally in respect of the time interval in relation to the reference anatomy image dataset.

When using a rectangular function it is expedient to apply it first, as it is equivalent to reducing the relevant anatomy image dataset.

An embodiment of the inventive method can be executed more quickly than known methods, as there is no need to calculate translation or rotation vectors.

The method can be used particularly advantageously for periodic movements, for example due to the rhythm of the heart or breathing. With periodic movements, an embodiment of the inventive method means that only measurement signals that were acquired in a specified phase of the cycle or a region around a specified phase are taken into account. The extent of the region is determined for example by the threshold value. It is therefore possible for example to generate one PET image dataset at the time point of breathing in and one at the time point of breathing out or the systole and diastole.

In principle, two fundamental situations are conceivable. The acquisition of a PET measurement signal takes approx. several microseconds and is shorter than the acquisition time for an anatomy image dataset. It should be noted here that only the acquisition of a PET measurement signal is so quick, not that of a PET image dataset calculated from a plurality of PET measurement signals.

The average time between the acquisition of two PET measurement signals is a function of the radioactivity and the quantity of the radionuclide. The following situations can therefore result:

During the acquisition of an anatomy image dataset one or more PET measurement signals are acquired. Then all the PET measurement signals are taken into account, regardless of whether there is one or more, during the reconstruction of the PET image dataset, if the similarity of the anatomy image dataset to the reference anatomy image dataset is above the predetermined threshold value.

It can however happen that no PET measurement signal occurs during the acquisition of an anatomy image dataset. The anatomy image dataset is then rejected, as it does not provide any information in respect of the reconstruction of the PET image dataset.

The similarity between two anatomy image datasets can be determined in a number of ways.

In a first alternative the similarity between two image datasets is determined by means of pattern recognition. In this process specified features of the anatomy image dataset are extracted (feature extraction) and compared with features obtained from the reference anatomy image dataset. Decision rules that are more complex than an individual threshold value are also possible here, in order to determine a similarity or non-similarity between an anatomy image dataset and the reference anatomy image dataset.

In a second alternative the similarity between two image datasets can be determined by means of a non-rigid registration. In this process either so-called landmarks can be taken into account or the image as a whole. The last-mentioned alternative is preferred, as the computation outlay is less, even though the registration quality may not be as optimal.

In a third alternative the similarity between two image datasets can be determined by way of a subtraction image. With this embodiment an anatomy image dataset is subtracted pixel by pixel from the reference anatomy image dataset or vice versa and the sum is determined from the reference image or the absolute values of the reference image. Absolute value formation may be necessary, as otherwise negative and positive difference values cancel one another out. If the sum is below a predetermined threshold value, there is a similarity. The similarity of two anatomy image datasets is therefore inversely proportional to the calculated sum.

In a fourth alternative it is possible to use a measure of correlation to determine the similarity of two anatomy image datasets.

The similarity can preferably only be determined in a predetermined, in particular automatically predetermined, region of the anatomy image datasets. With anatomy image datasets specifically a large region at the edge is often only filled with noise signal. This does not help to determine similarities and can therefore be ignored. The region used to determine a similarity can be obtained for example by means of mask formation in the reference anatomy image dataset or another anatomy image dataset. To this end a threshold value is predetermined and all the image elements or pixels, the numerical value of which is above the threshold value, are given the numerical value "1" or another value different from zero in the mask image. All the other image elements are assigned zero.

This threshold value can be determined automatically, for example from the maximum value of the anatomy image dataset or the mean value of all image elements or the mean value of all image elements above the noise signal, or even from the noise signal itself. The level of the noise signal can be determined from edge regions of the anatomy image dataset.

In addition the mask can also be a rectangle or a circle or another geometric shape such as an ellipse in the center of the image. The diameter or lengths of the sides and the precise positioning can be fixed or predetermined based on the examination protocol.

At least one periodicity of a periodic movement can preferably be determined based on further signals, in particular of an electrocardiogram (EKG), and can be taken into account when determining the parameters of the temporal weighting function. In particular with parallel magnetic resonance acquisitions of the heart for example there is always an EKG present on a patient. The signals of this EKG can then also be used to determine the periods or periodicity of the heartbeat. This information can be used for example to set the line width of a Gaussian weighting function or the interval and length of a number of rectangular functions as the weighting function in an optimized manner.

At least one embodiment of the present invention is also directed to a hybrid imaging modality. This comprises a positron emission tomography device and at least one second imaging modality, in particular a magnetic resonance device and/or a computed tomography device, as well as a control facility, which may be configured to perform at least one embodiment of the method.

The implementation of the abovementioned embodiments of the method in the control apparatus can be effected as software or as (permanently wired) hardware.

The advantageous embodiments of the inventive method correspond to corresponding embodiments of the inventive hybrid imaging modality, therefore please refer to the corresponding method features and their advantages to avoid unnecessary repetitions.

Figure 1:
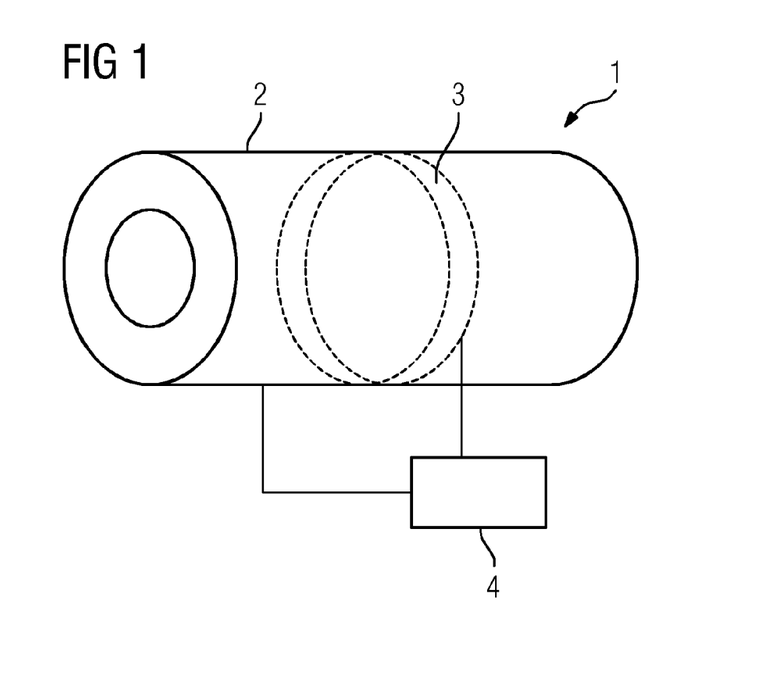
FIG. 1 shows an inventive hybrid imaging modality.

FIG. 1 shows a hybrid imaging modality 1 including a magnetic resonance device 2 with a detector ring 3 disposed therein and a control unit 4. Further components of the magnetic resonance device 2 such as gradient coils, excitation and detection coil, patient table as well as of the positron emission tomography device are not shown for the sake of clarity.

The detector ring 3 of the positron emission tomography device is disposed in the homogeneous region of the main magnetic field of the magnetic resonance device 2, so that simultaneous measurements with both imaging modalities are possible at the same time. The excitation coil, also referred to as the body coil, can be embodied as a unit with the detector ring in order not to restrict space for the patient unnecessarily.

This rigid structure registers the images acquired with the different imaging modalities simultaneously.

The described method is realized as software in the control unit 4. In particular it can be performed at the touch of a button after the patient has been positioned and a radiopharmaceutical has been administered.

Figure 2:
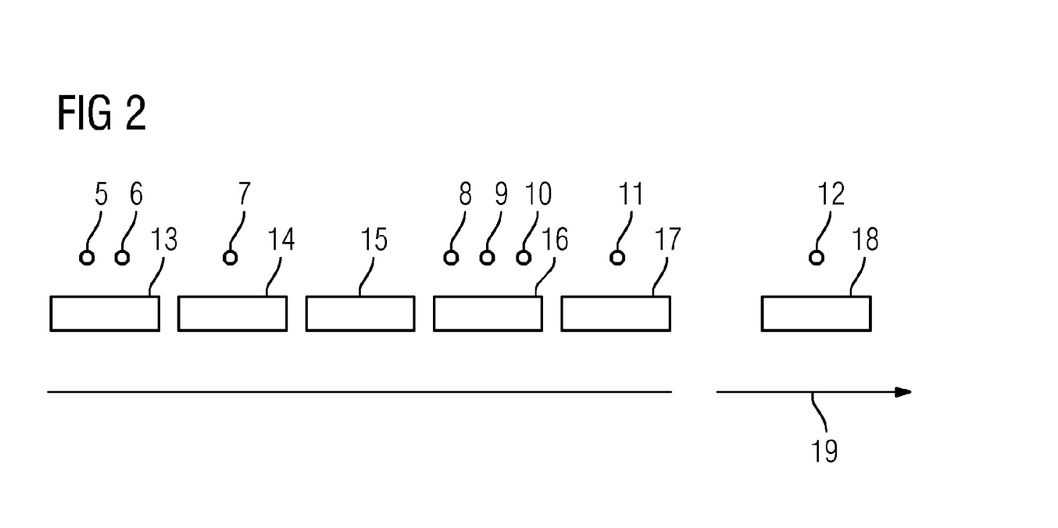
FIG. 2 shows PET measurement signals and anatomy image datasets in time order.

FIG. 2 shows the temporal relationship between PET measurement signals 5, 6, 7, 8, 9, 10, 11, and 12 and the magnetic resonance image datasets 13, 14, 15, 16, 17, and 18. These are shown over the axis 19, which is a time axis. The time required to acquire a magnetic resonance image dataset is in the region of several hundred milliseconds, even when using an extremely fast acquisition method such as TrueFisp. Therefore two or three PET measurement signals 5 and 6 or 8, 9 and 10 are detected during the acquisition of the magnetic resonance image datasets 13 and 16.

In contrast during the acquisition of the magnetic resonance image datasets 14, 17 and 18 only one PET measurement signal 7, 11 or 12 is detected in each instance. During acquisition of the magnetic resonance image dataset 15 however no annihilation event takes place. The magnetic resonance image dataset can be rejected as a function of the type of weighting. If weighting takes place based on similarity, with or without additional temporal weighting, the magnetic resonance image dataset 15 is not needed. With temporal weighting it only has to be ensured that the removal of the magnetic resonance image dataset does not result in a change to the temporal classification of the remaining magnetic resonance image datasets 13, 14, 16, 17 and 18.

In principle the PET measurement and the acquisition of the magnetic resonance image datasets can be performed for any length of time. The measurements can be terminated automatically after a predetermined number of counting events of the positron emission tomography device, if a maximum measurement period is exceeded or as a function of the signal to noise ratio of a positron emission tomography image dataset calculated from weighted PET measurement signals.

Figure 3:
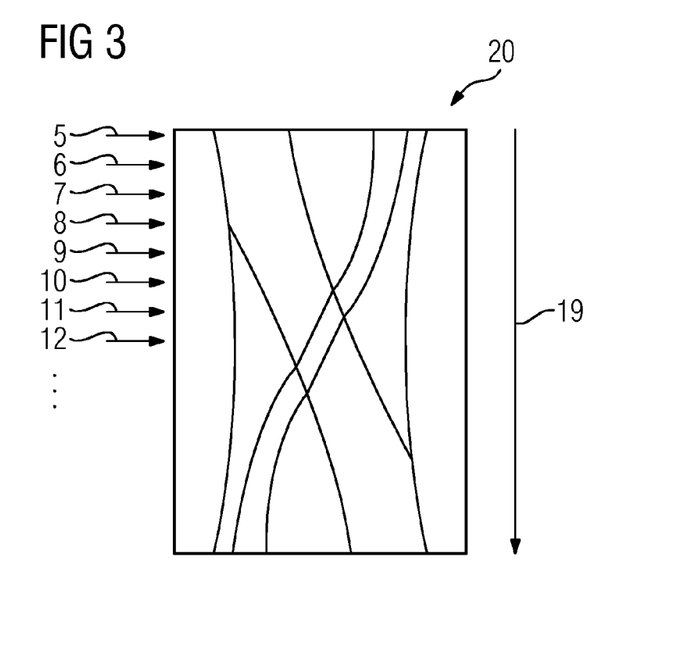
FIG. 3 shows a sinogram.

FIG. 3 shows a sinogram 20 of the PET measurement signals 5, 6, 7, 8, 9, 10, 11 and 12 and of further PET measurement signals. Each PET measurement signal represents a row in the sinogram 20. The PET measurement signals acquired as time progresses are lined up from top to bottom. As the PET measurement signals are in time order in the sinogram 20, a temporal weighting can also be performed directly on a sinogram 20 or the underlying data matrix.

Figure 4:
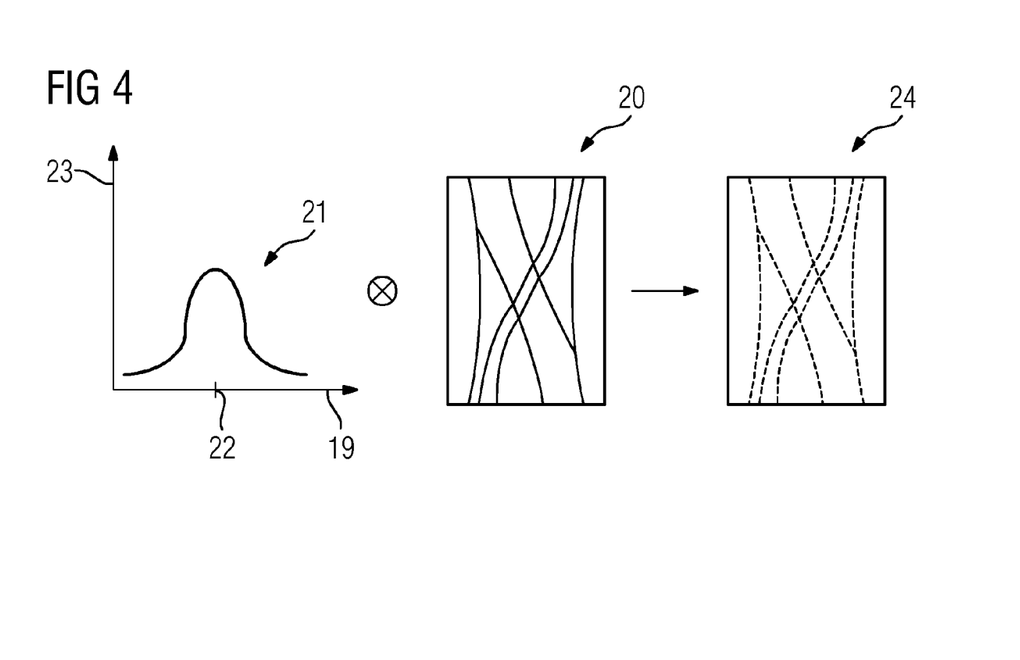
FIG. 4 shows a first weighting function.

FIG. 4 shows the application of a Gaussian function 21 to a sinogram 20. Here the center 22 of the Gaussian function 21 is assigned to the time point t', at which a PET image dataset is to be produced. It is not necessary for there to be a corresponding PET measurement signal or a row in the sinogram 20 for every point of the Gaussian function 21. If the time point t' is assigned to the last PET measurement signal or the last row of the sinogram 20, there is no counterpart to the right half of the Gaussian function 21. This is of course not a problem, as the Gaussian function can be restricted to a corresponding time region. The extent of the weighting is defined by means of the axis 23.

In the corresponding weighted sinogram 24 the parts weighted with a low weighting from the edge regions of the Gaussian function 21 are shown with broken lines. It is then possible to calculate a PET image dataset with fewer motion artifacts from this sinogram 24. Of course the calculation does not depend on a representation of the PET measurement signals as a sinogram.

Figure 5:
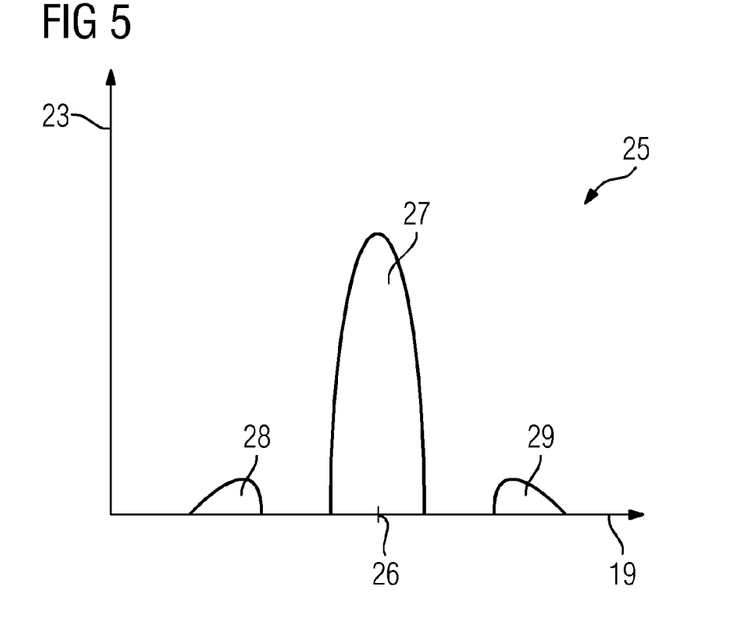
FIG. 5 shows a second weighting function.

FIG. 5 shows a weighting function 25, which was obtained from similarities between anatomy image datasets. The most similar anatomy image datasets are found around the time point 26, which represents the reference time point t', which is why the highest function values are located in the central region 27 of the weighting function 25. The axis 23 again indicates the extent of the weighting.

Anatomy image datasets with an adequate similarity, in other words a similarity above one or more threshold values, are also still found in side regions 28 and 29 somewhat removed from the central region 27. As the similarity of the anatomy image datasets associated with the side regions to the reference anatomy image dataset is less than in the central region 27, the function value is correspondingly lower in each instance.

Figure 6:
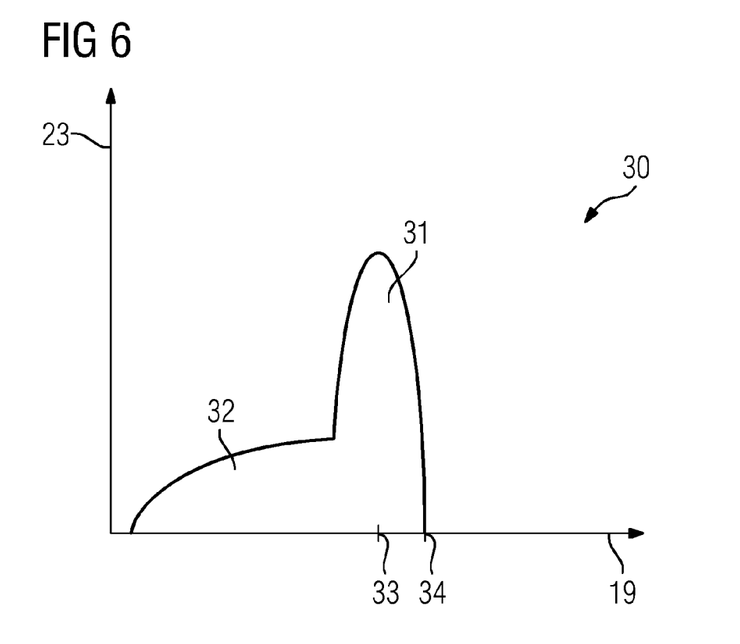
FIG. 6 shows a third weighting function.

FIG. 6 shows an alternative weighting function 30. The similarities of the anatomy image datasets to a reference anatomy image dataset are greater in the central region 31 than in the side arm 32. The time point 33 corresponds to the selected time point t', for which the PET image dataset is to be calculated.

At time point 34 the examination object moved in an involuntary and non-periodic manner, with the result that the similarities determined for the time period thereafter all move below the threshold value(s) and the corresponding PET measurement signals are therefore excluded.

Figure 7:
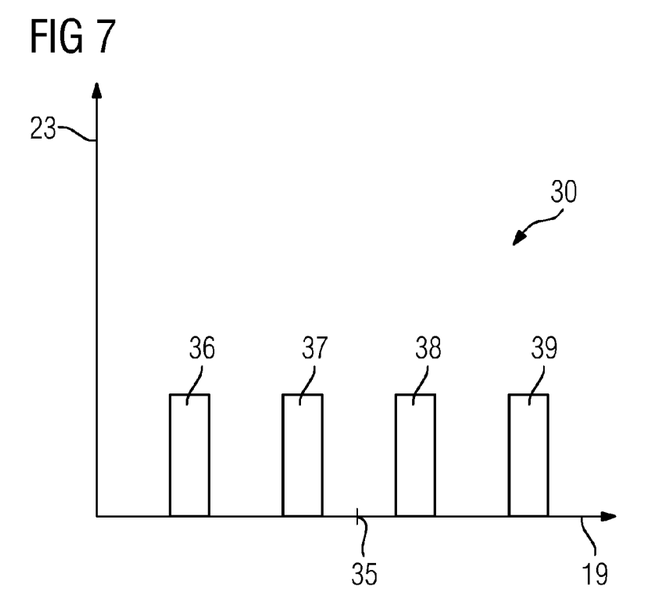
FIG. 7 shows a fourth weighting function.

FIG. 7 shows the application of a rectangular function for periodic movements. The similarities between a number of anatomy image datasets are used here to establish movement periodicities for example of the breathing and heartbeat of an examination object. The periodicities can then be used to specify rectangular windows 36, 37, 38 and 39 from a predeterminable time point 35, from which PET measurement signals can be taken into account.

A further temporal weighting in the form of a Gaussian function can also be multiplied onto these PET measurement signals, as described above in relation to FIG. 4.

Figure 8:
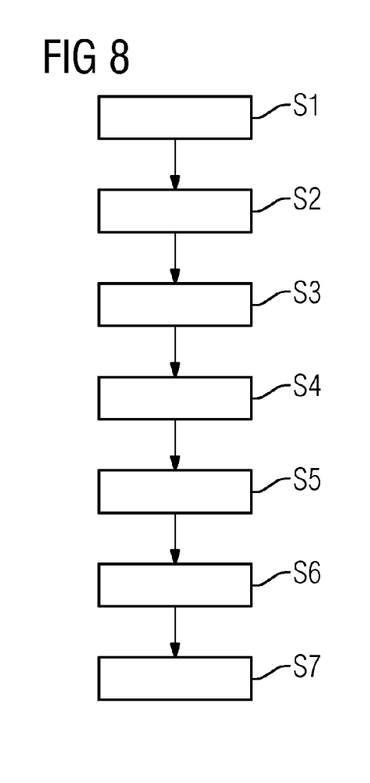
FIG. 8 shows a flow diagram of n embodiment of the inventive method.

FIG. 8 shows a flow diagram for producing a PET image dataset. In step S1 a patient is introduced into the hybrid imaging modality 1 and all the necessary steps to prepare for measurement, for example shimming the magnetic field of a magnetic resonance scanner, are performed. In step S2 measurement data acquisition is started simultaneously by means of the positron emission tomography device and the magnetic resonance device, with the time point of the acquisition of the PET measurement signal and also of a magnetic resonance image dataset being stored.

In step S3 the raw data acquired using the magnetic resonance device is processed to produce image datasets, in order to be able to perform a similarity calculation thereon.

In the following step S4 a time point t' is to be predetermined by a user or automatically, at which a PET image dataset is to be determined.

The reference anatomy image dataset is established from time point t', its similarities to the other anatomy image datasets being determined (step S5). In this process the following method can be applied to optimize computation power:

Starting from the reference anatomy image dataset the anatomy image datasets closest in time are used first. If the similarity of the anatomy image datasets to the reference anatomy image dataset decreases as the time interval increases, in particular to below a termination threshold value, the determination of similarities is terminated and the similarity values are set to zero. This termination procedure can be used for all embodiments.

In step S6 the PET measurement signals are additionally weighted with a Gaussian function.

In the last step S7 a PET image dataset is determined from the twice weighted PET measurement signals. The weightings mean that the motion artifacts therein are minimized.

It also goes without saying that features described with reference to individual embodiments can also be realized in other embodiments or forms, unless specifically described otherwise or impossible for technical reasons.

What is claimed is:

1. A method for generating a positron emission tomography (PET) or single-photon emission computed tomography (SPECT) image dataset for an at least partially moving examination object, the method comprising:
   acquiring a plurality of PET or SPECT measurement signals from an examination region of the examination object;
   acquiring a plurality of anatomy image datasets that show the examination region using a second imaging modality, the plurality of anatomy image datasets being acquired simultaneously with the acquired plurality of measurement signals;
   selecting a reference anatomy image dataset from the plurality of anatomy image data sets;
   applying a temporal weighting function to the plurality of PET or SPECT measurement signals;
   removing at least one of the plurality of anatomy image datasets when no corresponding measurement signal is acquired during a time period of acquiring the at least one of the plurality of anatomy image data sets; and
   generating at least one of a PET or SPECT image dataset based on the temporally weighted plurality of measurement signals, wherein the temporal weighting function is decreased as a measurement signal of the PET or SPECT becomes more distant from the reference anatomy image data set in time.

2. The method of claim 1, further comprising determining a similarity between the anatomy image datasets using pattern recognition.

3. The method of claim 1, further comprising determining a similarity between the anatomy image datasets via a non-rigid registration.

4. The method of claim 1, further comprising determining a similarity between the anatomy image datasets is determined via a subtraction image.

5. The method of claim 1, wherein at least one periodicity of a periodic movement of the examination object is determined based on further signals and wherein a parameter of the temporal weighting function is taken into account during the determination.

6. The method of claim 1, further comprising determining a similarity between the anatomy image datasets, wherein the similarity is only determined in a designated region of the anatomy image datasets.

7. The method of claim 1, further comprising determining a similarity between the anatomy image datasets, wherein the determination of the similarity of the anatomy image datasets is started with the anatomy image datasets closest in time to the reference anatomy image dataset.

8. The method of claim 1, wherein a rectangular function or a Gaussian function is used as the temporal weighting function.

9. The method of claim 1, wherein a computed tomography device or a magnetic resonance device is used as the second imaging modality.

10. A hybrid imaging modality, comprising:
    a positron emission tomography (PET) device or a single-photon emission computed tomography (SPECT) device;
    at least one second imaging modality; and
    a control unit, configured to
       acquire, via the PET device or the SPECT device, a plurality of measurement signals from an examination region,
       acquire, via the at least one second imaging modality, a plurality of anatomy image datasets that show the examination region, the plurality of anatomy image datasets being acquired simultaneously with the acquired measurement signals,
       determine a reference anatomy image dataset from among the plurality of anatomy image datasets, the reference anatomy image data set being an anatomy image dataset acquired at a first time point,
       determine a similarity between the reference anatomy image dataset and at least one other anatomy image dataset acquired at a different time point using the second image modality, and
       apply a temporal weighting function to the plurality of measurement signals acquired from the PET device or the SPECT device based on the similarity between the reference anatomy image dataset and the other anatomy image dataset, and remove at least one of the plurality of anatomy image datasets when no corresponding measurement signal is acquired during a time period of acquiring the at least one of the plurality of anatomy image data sets, generate a PET or SPECT image dataset based on the temporal weighting function.

11. The method of claim 5, wherein the at least one periodicity of a periodic movement is determined based on further signals of an electrocardiogram (EKG).

12. The method of claim 2, wherein the similarity is only determined in a designated region of the anatomy image datasets.

13. The method of claim 2, wherein the determination of the similarity of the anatomy image datasets is started with the anatomy image datasets closest in time to the reference anatomy image dataset.

14. The method of claim 3, wherein the similarity is only determined in a designated region of the anatomy image datasets.

15. The method of claim 3, wherein the determination of the similarity of the anatomy image datasets is started with the anatomy image datasets closest in time to the reference anatomy image dataset.

16. The method of claim 4, wherein the similarity is only determined in a designated region of the anatomy image datasets.

17. The method of claim 4, wherein the determination of the similarity of the anatomy image datasets is started with the anatomy image datasets closest in time to the reference anatomy image dataset.

18. The method of claim 2, wherein a rectangular function or a Gaussian function is used as the temporal weighting function.

19. The method of claim 2, wherein a computed tomography device or a magnetic resonance device is used as the second imaging modality.

20. The method of claim 3, wherein a rectangular function or a Gaussian function is used as the temporal weighting function.

21. The method of claim 3, wherein a computed tomography device or a magnetic resonance device is used as the second imaging modality.

22. The method of claim 4, wherein a rectangular function or a Gaussian function is used as the temporal weighting function.

23. The method of claim 4, wherein a computed tomography device or a magnetic resonance device is used as the second imaging modality.

24. The hybrid imaging modality of claim 10, wherein the at least one second imaging modality includes at least one of a magnetic resonance device, a computed tomography device, an x-ray device and an ultrasound device.

25. The hybrid imaging modality of claim 10, wherein the similarity between the anatomy image datasets is determined using pattern recognition.

26. The hybrid imaging modality of claim 10, wherein the similarity between the anatomy image datasets is determined via a non-rigid registration.

27. The hybrid imaging modality of claim 10, wherein the similarity between the anatomy image datasets is determined via a subtraction image.

28. A method for generating a positron emission tomography (PET) or single-photon emission computed tomography (SPECT) image dataset for an at least partially moving examination object, the method comprising:

acquiring a plurality of PET measurement signals or SPECT measurement signals from an examination region;

acquiring a plurality of anatomy image datasets that show the examination region using a second imaging modality simultaneously with the acquired plurality of measurement signals;

determining a similarity between a reference anatomy image dataset acquired at a first time point using the second imaging modality and at least one anatomy image dataset acquired at a different time point, the similarity between the anatomy image datasets being determined by extraction of a specific feature acquired in an anatomy image dataset and comparing the extracted feature with a feature acquired in the reference anatomy image dataset, removing at least one of the plurality of anatomy image datasets when no corresponding measurement signal is acquired during a time period of acquiring the at least one of the plurality of anatomy image data sets, and generating at least one of the PET or SPECT image dataset based on the determined similarity of the extracted features.

* * * * *